(12) United States Patent
Turcott

(10) Patent No.: US 9,022,030 B2
(45) Date of Patent: May 5, 2015

(54) METHODS, SYSTEMS AND DEVICES FOR MONITORING RESPIRATORY DISORDERS

(75) Inventor: Robert G. Turcott, Portola Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 1088 days.

(21) Appl. No.: 12/709,336

(22) Filed: Feb. 19, 2010

(65) Prior Publication Data

US 2010/0152560 A1  Jun. 17, 2010

Related U.S. Application Data

(62) Division of application No. 10/897,372, filed on Jul. 21, 2004, now Pat. No. 7,690,378.

(51) Int. Cl.
| | | |
|---|---|---|
| F16K 31/02 | (2006.01) | |
| A61B 5/08 | (2006.01) | |
| A61B 5/1455 | (2006.01) | |
| A61B 5/00 | (2006.01) | |

(52) U.S. Cl.
CPC .......... *A61B 5/0816* (2013.01); *A61B 5/14551* (2013.01); *A61B 5/411* (2013.01); *A61B 5/415* (2013.01); *A61B 5/4818* (2013.01)

(58) Field of Classification Search
USPC ............. 128/200.24, 204.18, 204.21, 204.23, 128/204.26; 600/508, 513, 526; 607/17
See application file for complete search history.

(56) References Cited

U.S. PATENT DOCUMENTS

| | | | |
|---|---|---|---|
| 4,506,666 A | 3/1985 | Durkan | |
| 4,715,367 A | 12/1987 | Crossley | |
| 4,809,697 A | 3/1989 | Causey, III et al. | |
| 4,815,469 A | 3/1989 | Cohen et al. | |
| 4,830,008 A | 5/1989 | Meer | |
| 4,869,254 A | 9/1989 | Stone et al. | |
| 4,944,299 A | 7/1990 | Silvian | |
| 5,078,136 A | 1/1992 | Stone et al. | |
| 5,146,918 A | 9/1992 | Kallok et al. | |
| 5,174,287 A | 12/1992 | Kallok et al. | |
| 5,178,156 A | 1/1993 | Takishima et al. | |
| 5,215,082 A | 6/1993 | Kallok et al. | |
| 5,238,006 A | 8/1993 | Markowitz | |
| 5,277,193 A | 1/1994 | Takishima et al. | |
| 5,385,144 A | 1/1995 | Yamanishi et al. | |
| 5,483,969 A | 1/1996 | Testerman et al. | |
| 5,522,862 A | 6/1996 | Testerman et al. | |

(Continued)

FOREIGN PATENT DOCUMENTS

| | | |
|---|---|---|
| EP | 0505195 B1 | 11/1997 |
| WO | 9841146 A1 | 9/1998 |
| WO | 0176459 A2 | 10/2001 |
| WO | 0176459 A3 | 10/2001 |
| WO | 02087433 A1 | 11/2002 |

OTHER PUBLICATIONS

NonFinal Office Action, mailed Dec. 24, 2008: U.S. Appl. No. 10/897,372.

(Continued)

*Primary Examiner* — Victoria J Hicks

(57) ABSTRACT

Methods, systems and devices are provided for monitoring respiratory disorders based on monitored factors of a photoplethysmography (PPG) signal that is representative of peripheral blood volume. The monitored factors can be respiratory effort as well as respiratory rate and/or blood oxygen saturation level. The systems and devices may or may not be implanted in a patient.

18 Claims, 10 Drawing Sheets

(56) References Cited

U.S. PATENT DOCUMENTS

| | | | |
|---|---|---|---|
| 5,540,733 | A | 7/1996 | Testerman et al. |
| 5,549,655 | A | 8/1996 | Erickson |
| 5,591,216 | A | 1/1997 | Testerman et al. |
| 6,015,388 | A | 1/2000 | Sackner et al. |
| 6,126,611 | A | 10/2000 | Bourgeois et al. |
| 6,132,384 | A | 10/2000 | Christopherson et al. |
| 6,240,316 | B1 | 5/2001 | Richmond et al. |
| 6,251,126 | B1 | 6/2001 | Ottenhoff et al. |
| 6,269,269 | B1 | 7/2001 | Ottenhoff et al. |
| 6,375,623 | B1 | 4/2002 | Gavriely |
| 6,409,675 | B1 | 6/2002 | Turcott |
| 6,480,733 | B1 | 11/2002 | Turcott |
| 6,491,639 | B1 | 12/2002 | Turcott |
| 6,600,949 | B1 | 7/2003 | Turcott |
| 6,709,402 | B2 * | 3/2004 | Dekker ........................ 600/529 |
| 6,731,967 | B1 | 5/2004 | Turcott |
| 6,869,402 | B2 * | 3/2005 | Arnold ......................... 600/500 |
| 7,194,306 | B1 * | 3/2007 | Turcott ........................... 607/17 |
| 7,324,848 | B1 * | 1/2008 | Turcott ........................... 607/17 |
| 2002/0002327 | A1 | 1/2002 | Grant et al. |
| 2002/0029000 | A1 | 3/2002 | Ohsaki et al. |
| 2002/0049479 | A1 | 4/2002 | Pitts |
| 2002/0193679 | A1 | 12/2002 | Cho et al. |
| 2002/0193697 | A1 * | 12/2002 | Cho et al. ..................... 600/529 |

OTHER PUBLICATIONS

NonFinal Office Action, mailed Apr. 1, 2009: U.S. Appl. No. 10/897,372.

Notice of Allowance, mailed Jan. 13, 2010: U.S. Appl. No. 10/897,372.

Nilsson, Lena MD et al., "Monitoring of Respiratory Rate in Postoperative Care using a New Photoplethysmographic Technique," J Clin Monit 2000:16:309-315.

Johansson, Anders et al., "Monitoring of Heart and Respiratory Rates in Newborn infants using a new Photoplethysmographic Technique," J Clin Monit 1999:15:461-467.

Davis, C. et al., "A New Fibre Optic Sensor for Respiratory Monitoring," Australas Phys Eng Sci Med. 1997;20(4):214-219 (Abstract).

Vegfors, M. et al., "Presentation and Evaluation of a New Optical Sensor for Respiratory Rate Monitoring," Int J Clin Monit Comput. Aug. 1994;11(3):151-156 (Abstract).

Dorlas, J.C. et al., "Photo-electric Plethysmography as a Monitoring Device in Anaesthesia. Application Interpretation." BR J. Anaesth. May 1985;57(5):524-530 (Abstract).

Defaye, P. MD et al., "Permanent Monitoring of Sleep-Disordered Breathing by a Pacemaker," PACE. 2003;26 (Abstract).

Scharf, C. MD et al., "Automatic Algorithm for Sleep Apnea Detection Using a Pacemaker Impedance Sensor," PACE, vol. 26, 2003 (Abstract).

Shalaby, Alaa A. MD. et al., "Automated Detection of Sleep Apnea Using a Pacemaker Impedance Sensor," PACE. 2003;26 (Abstract).

Gunn, S.R. MD et al., "Implications of Arterial Pressure Variation in Patients in the Intensive Care Unit," Curr Opin Crit Care. 2001;7:212-217.

Watanabe, Takuya et al., "The Relationship Between Esophageal Pressure and Apnea Hypopnea Index in Obstructive Sleep Apnea-Hypopnea Syndrome," Sleep Research Online. 2000;3(4):169-172.

Landon Chris MD FAAP FCCP, "Respiratory Monitoring: Advantages of Inductive Plethysmography Over Impedance Pneumography," VivoMetrics, VMLA-039-02:1-7.

The Vancouver Sleep & Breathing Centre, "Sleep Study," http://www/sleep-breathing.bc.ca/sleep.htm (printed May 24, 2004), pp. 1-5.

"OSA—Polysomnography," http://classes.kumc.edu/cahe/respcared/cybercas/sleepapnea/trenpoly.html (printed May 24, 2004), pp. 1-5.

"Obstructive Sleep Apnea," http://sleepmed.bsd/uchicago.edu/osa.html (printed May 24, 2004), pp. 1-7.

* cited by examiner

METHODS, SYSTEMS AND DEVICES FOR MONITORING RESPIRATORY DISORDERS

CROSS REFERENCE TO RELATED APPLICATIONS

This application is a division of U.S. patent application Ser. No. 10/897,732, filed Jul. 21, 2004, now U.S. Pat. No. 7,690,378.

FIELD OF THE INVENTION

The present invention relates to methods, systems and devices for monitoring, diagnosing and possibly treating respiratory disorders.

BACKGROUND OF THE INVENTION

Millions of people suffer from various types of respiratory disorders that cause abnormal breathing patterns. Examples of such respiratory disorders include sleep apnea, asthma and emphysema, each of which is briefly discussed below.

Sleep Apnea

Sleep apnea is a disease in which breathing ceases during sleep. It is associated with increased mortality and morbidity, including sudden death, heart failure, hypertension, stroke, and neuropsychiatric and behavioral disturbances.

Obstructive sleep apnea (OSA) is a very common type of sleep apnea, which often affects obese persons. This disorder occurs when a person's upper airway becomes partially or completely blocked, causing breathing to be interrupted intermittently during sleep. The blocked or obstructed breathing prevents deep stages of sleep, often resulting in daytime drowsiness.

There are a number of different reasons that the upper airway can become obstructed. For example, obstruction can result from upper airway abnormalities, such as enlarged tonsils or enlarged adenoids. Other upper airway abnormalities may result from obesity, an abnormally wide neck, or from an anatomically narrowed upper airway. Such abnormalities often result in excess tissue within the throat, which cause the upper airway to become blocked when throat muscles relax during sleep.

The most commonly prescribed treatment for obstructive sleep apnea is continuous positive airway pressure (CPAP). In CPAP treatment, the patient sleeps wearing a facial or nasal mask that delivers air pressure that stents the airway open. For many patients, CPAP therapy works well. However, many other patients find the masks very uncomfortable, preventing them from sleeping, and often causing them to remove the masks and thus avoid their treatment. Further, CPAP therapy has had no effect in some patients and has even resulted in increased episodes of apnea in some patients.

Other conventional treatments for obstructive sleep apnea include use of anti-depressant drugs, such as protriptyline (often marketed as Vivactil™ or Triptil™). In addition to not always being effective, protriptyline has a number of side effects, such as dizziness, drowsiness, dryness of mouth, headaches, increased appetite, nausea, tiredness or weakness, unpleasant taste and weight gain. Less frequent side effect include diarrhea, heartburn, increased sweating, trouble in sleeping, and vomiting. There are also rare but more severe side effects, such as blurred vision, confusion or delirium, constipation (especially in the elderly), decreased sexual ability (more common with amoxapine and clomipramine), difficulty in speaking or swallowing, eye pain, fainting, fast or irregular heartbeat (pounding, racing, skipping) and hallucinations.

OSA can also be treated surgically. However the costs are high, the risks are high, and the success rates vary greatly depending on the procedure and the experience and skills of the surgeon. Additionally, the surgery can affect speech and the ability to swallow.

Another type of sleep apnea is central sleep apnea (CSA), which is a different than OSA. CSA is a neurological disorder that results from problems with breathing control mechanisms, as opposed to airway blockage (as with OSA). CSA can occur, for example, due to the portion of the brain that controls breathing failing to signal the body to breathe. Persons suffering from CSA are often awoken during sleep, leading to sleep deprivation, and thus, daytime drowsiness.

While CPAP therapy is sometime used with patients suffering from CSA, other types of mechanical ventilation are often the only treatment available to ensure continued breathing. Unfortunately, complications may result from prolonged mechanical ventilation.

A further type of respiratory disorder that occurs during sleep is hypopnea, which is generally defined as decrease in airflow by at least 50% for ten seconds or more. In this document, hypopnea will be considered a type of sleep apnea, even though shallow breathing continues during hypopnea.

Diagnosis of sleep apnea is not simple because there can be many different reasons for disturbed sleep. While there are various tests for evaluating a person for sleep apnea, most are very expensive and sometime inconclusive. Typically a patient is required to sleep overnight at a sleep treatment center, so that the patient can be monitored and diagnosed. Such overnight stays are typically very expensive and are sometimes inconclusive because the patient either did not exhibit their normal sleep patterns or because the patient does not experience sleep apnea every night. Additionally, since treatments for OSA and CSA are often different, it is important that the type of sleep apnea be accurately diagnosed.

As is evident from the above description, there is the need for improved systems and methods for diagnosing sleep apnea and treating sleep apnea. This will allow appropriate treatments to be prescribed. Further, even after a treatment is being provided, it is important to chronically monitor a person's breathing in order to determine if specific treatments are working, to determine if treatments can be fine tuned and/or to determine if alternative treatments should be used.

Asthma

Asthma is a disease of the respiratory system, which includes a person's nose, mouth, trachea, lungs, and air tubes or airways that connect the nose and mouth with the lungs (these tubes are called bronchi and bronchioles). When a person breathes, the muscles that are wrapped around the airways are very loose and relaxed. Since the lining inside the airways is very thin, the relaxed state of the muscles allows the airways to open widely so that air easily passes in and out of the small air sacs (called alveoli) that make up the lungs. Breathing includes the moving of air in and out of the lungs.

During an asthma attack, the muscles around the airways tighten, or "spasm" and the lining inside the airways swell or thicken, and become blocked with thick mucous. This makes the airways much thinner than usual so it is harder to move air in and out of the air sacs, making it difficult to breathe. During an asthma attack, it is actually harder to breathe out than it is to breathe in. This means that during an asthma attack, it takes much longer to breathe out (expire) than it does to breathe in (inspire). Since it is so hard to breathe out during an asthma attack, more and more air gets trapped inside the lungs making a person feel like they can't breathe in or out.

There are different types of asthma, including allergy-induced asthma and activity-induced asthma. Additionally, there are different severities of asthma, including mild, intermittent, moderate and severe asthma. Different types of asthma and different severities of asthma may be treated in different manners. Accordingly, it is desirable to be able to obtain information that is useful in diagnosing the type and/or severity of a person's asthmatic condition. Further, even after a person's asthma has been diagnosed, the proper treatment needs to be provided. Treatments include medication, altering diet and/or altering activities. However, even if two different people have the same symptoms, they may not react in the same way to the same treatment. That is, not all types of treatments work well with all people. Accordingly, even after a treatment regimen has been prescribed, it is important to chronically monitor a person's breathing in order to determine if specific treatments are working, to determine if treatments can be fine tuned and/or to determine if alternative treatments should be used.

Emphysema

Emphysema is an abnormal condition of the lungs, which belongs to a group of conditions called Chronic Obstructive Pulmonary Disease (COPD). Emphysema, which generally develops gradually over a number of years, typically results in an increased shortness of breath, not relieved by sitting upright, and a chronic cough. The shortness of breath is generally worse on exertions such as walking up a flight of stairs or eating a big meal. Eventually, breathing becomes harder and harder causing fatigue, weakness, and weight loss. Emphysema can result for various reasons, such as chronic bronchitis, or chronic irritation to the lungs by dust, pollution, and cigarette smoking. Such chronic irritations cause the tiny air sacs in the lungs to loose their elasticity and become distended, causing inhaled air to become trapped in the air sacs. As with most respiratory disorders, there is no cure for emphysema but there are numerous treatments that can help relieve the shortness of breath.

There are different causes and severities for emphysema, each of which can be treated in multiple different manners. Accordingly, it is desirable to be able to obtain information that is useful in diagnosing the type and/or severity of the emphysema. Further, even after a treatment is being provided, it is important to chronically monitor a person's breathing in order to determine if specific treatments are working, to determine if treatments can be fine tuned and/or to determine if alternative treatments should be used.

As can be appreciated from the above description, it would be useful to provide a means for temporarily and/or chronically monitoring various breathing disorders in order to properly diagnose the disorders, treat the disorders, and monitor the treatment of the disorders.

SUMMARY

What are described herein are systems and methods to monitor respiratory disorders based on monitored factors of a photoplethysmography (PPG) signal that is representative of peripheral blood volume. Depending on the embodiment, the device that is used to produce the PPG signal may or may not be implanted in a patient.

In accordance with an embodiment, respiratory effort is monitored based on the PPG signal. Respiratory effort can be monitored by determining amplitudes of the PPG signal. In accordance with an embodiment, an exacerbation of the respiratory disorder is detected based on the monitored respiratory effort.

In accordance with embodiments, respiratory rate and/or blood oxygen saturation is also monitored based on the PPG signal. This enables an exacerbation of the respiratory disorder to be detected based on the monitored respiratory effort as well as the monitored respiratory rate and/or blood oxygen saturation.

In accordance with an illustrative embodiment, the respiratory disorder being monitored is sleep apnea, and thus, the PPG signal is produced while a patient, whose respiratory disorder is being monitored, is sleeping. An episode of sleep apnea can be detected based on the monitored respiratory effort. Respiratory rate and/or blood oxygen saturation can also be monitored, based on the PPG signal, while the patient is sleeping. This enables an episode of sleep apnea to be detected based on the monitored respiratory effort as well as the monitored respiratory rate and/or blood oxygen saturation level.

In accordance with other illustrative embodiments, the sleeping patient can be stimulated in response to detecting an episode of sleep apnea. This can include producing at least one of an audible stimuli, a vibrating stimuli and an electrical stimuli. Alternatively, or additionally, an alert indicator may be triggered in response to detecting an episode of sleep apnea.

Embodiments are also directed to diagnosing whether a patient suffers from obstructive sleep apnea (OSA) or central sleep apnea (CSA) based on the monitored respiratory effort.

In accordance with an embodiment, the respiratory disorder being monitored is asthma. An asthmatic episode can be detected based on the monitored respiratory effort. If respiratory rate and/or blood oxygen saturation are also monitored based on the PPG signal, then an asthmatic episode can be detected based on the monitored respiratory effort as well as the monitored respiratory rate and/or blood oxygen saturation level.

Other features and advantages will appear from the following description in which the preferred embodiments have been set forth in detail, in conjunction with the accompanying drawings and claims.

DETAILED DESCRIPTION

As a person breathes, the intrathoracic pressure, which relates to pressure inside the chest, changes accordingly. More specifically, as a person inhales during breathing, the chest expands and there is a slight decrease in intrathoracic pressure, relative to atmospheric pressure, which drives air into the lungs. With exhalation, there is an increase in intrathoracic pressure that forces air out of the lungs. These changes in intrathoracic pressure also cause subtle changes in the way blood returns to the heart through veins, and is pumped from the heart through arteries.

In other words, changes in intrathoracic pressure that results from respiration effect how quickly blood will return from veins into the right side of the heart. As a person inhales, there is lower pressure in the chest as compared to the periphery (e.g., limbs), due to the decrease in intrathoracic pressure. This pressure gradient causes blood to flow back to the chest. Conversely, when a person exhales, there is a higher pressure in the chest than the periphery due to the increase in intrathoracic pressure. This causes more resistance to blood return from the periphery. In this manner, venous blood pressure varies as a person breathes. Arterial blood pressure also changes with respiration, as can be seen using a pressure monitor, though by a slightly different mechanism.

Embodiments of the present invention observe changes in blood volume in order to monitor respiration. More specifically, in accordance with embodiments of the present invention, photoplethysmography (PPG) devices are used alone or in combination with other devices to monitor respiration. As will be discussed in further detail below, the PPG device (and other devices) can either be an invasive (i.e., implanted) or a non-invasive device.

Exemplary PPG Signal

Figure 1:
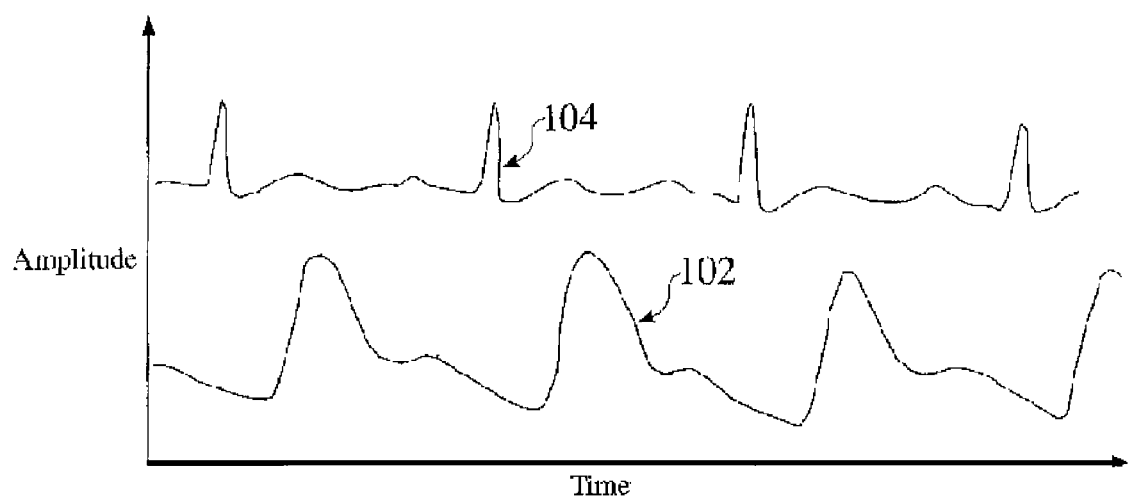
FIG. 1 illustrates exemplary plethysmography and electrocardiogram signals.

FIG. 1 illustrates an exemplary photoplethysmography (PPG) signal 102 produced using a PPG device (also known as a PPG sensor). For timing reference, an electrocardiogram (ECG) signal 104 is also illustrated. Waveform 102 provides a measure of the volume of the arterial vasculature. A measure of arterial pulse amplitude is derived from it. A few tens to a few hundreds of milliseconds after the QRS complex, the plethysmography voltage reaches a minimum and starts to increase. This is due to the increasing blood volume in the arterioles as the systolic pulse reaches the periphery. The delay is influenced by the distance that the sensor is placed from the heart. It requires approximately 100 msec for the waveform to reach its maximum. The excursion from minimum to maximum represents the arterial pulse amplitude. During diastole, the recoil of the elastic arterial vessels continues to force blood through the capillaries, so that blood flows through the capillary bed throughout the entire cardiac cycle. Not obvious in this figure because of the time scale is the influence of venous blood volume on the PPG waveform. As venous blood volume is modulated by respiration, as described above, the amount of light absorbed by the tissue is also modulated. This is detectable as a change in the amplitude of the PPG waveform.

Exemplary Plethysmography Devices

A photoplethysmography device (PPG) (also called a pseudoplethysmography or photoelectric plethysmography device) includes a light detector and a light source. The PPG device utilizes the transmission or reflection of light to demonstrate the changes in blood perfusion. Such devices are typically used in the cardiology department or intensive care department of a hospital or in a clinic for diagnostic purposes related to vascular surgery. A PPG device is also referred to, herein, simply as a plethysmography device.

Figure 2A:
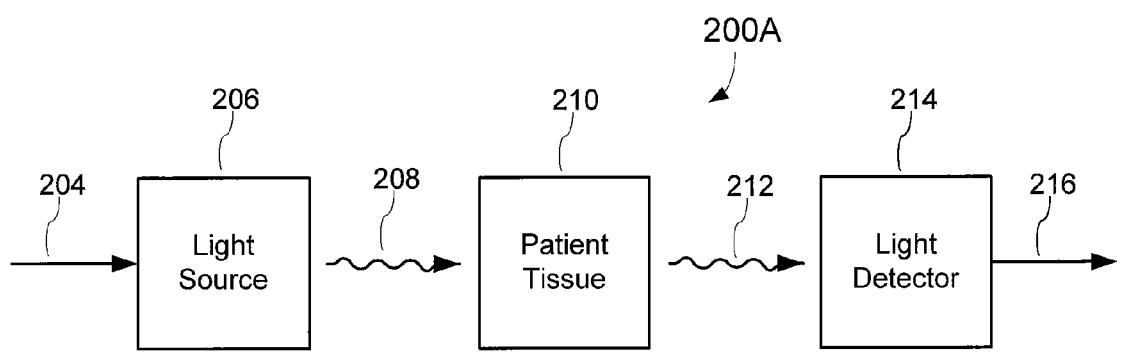
FIG. 2A is a block diagram illustrating an exemplary conventional photoplethysmography (PPG) device.
Figure 2B:
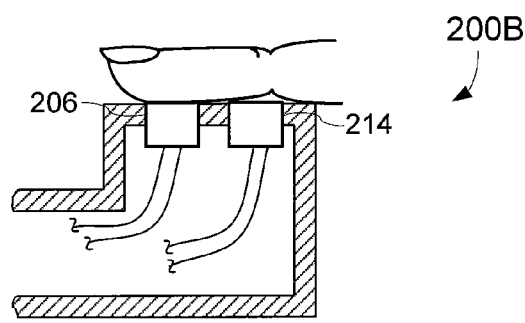
FIG. 2B is a simplified mechanical diagram illustrating a portion of an exemplary PPG device.
Figure 2C:
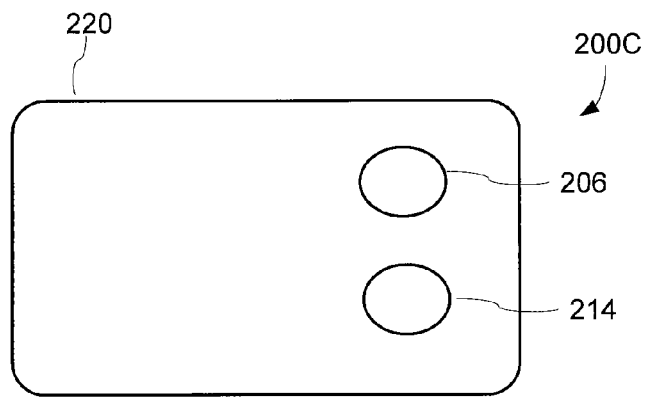
FIG. 2C is a simplified mechanical diagram illustrating an exemplary implantable PPG device.

A block diagram 200A of an exemplary PPG device is shown in FIG. 2A. An exemplary mechanical arrangement 200B for a noninvasive (i.e., not implanted) PPG device is shown in FIG. 2B. An exemplary mechanical arrangement 200C for a chronically implantable PPG device is shown in FIG. 2C.

The PPG device includes a light source 206 and a light detector 214. In one example, the light source 206 is a light-emitting diode (LED), although in alternative models an incandescent lamp or laser diode can be used as the light source. Referring to FIG. 2A, light source 206 outputs a transmit light signal 208 that is transmitted through and/or reflected by (depending on the embodiment) patient tissue 210. A receive light signal 212 is received by light detector 214. Light detector 214 can include, for example, a photoresistor excited by a constant current source. Changes in light intensity cause proportional changes in the resistance of the photoresistor. Since the current through the photoresistor is constant in this example, the resistance changes produce a varying analog voltage light detection signal 216. This varying analog voltage light detection signal 216, which is a plethysmography signal, is typically filtered and amplified and then converted to a digital signal using an analog to digital converter (not shown). The light detector can, for example, alternatively include a photodiode, phototransistor, photodarlington or avalanche photodiode. Light detectors are often also referred to as photodetectors or photocells.

Light may be transmitted through a capillary bed such as in an earlobe or finger tip. As arterial pulsations fill the capillary bed and pre-capillary arterioles, the changes in volume of the blood vessels modify the absorption, reflection and scattering of the light. Stated another way, an arterial pulse in, for example, a finger tip, or earlobe, causes blood volume to change, thereby changing the optical density of the tissue. Therefore, the arterial pulse modulates the intensity of the light passing through the tissue.

PPG devices may operate in either a transmission configuration or a reflection configuration. In the transmission configuration, light source 206 and light detector 214 face one another and a segment of the body (e.g., a finger or earlobe) is interposed between source 206 and detector 214. In the reflection configuration, light source 206 and light detector 214 are mounted adjacent to one another, e.g., on the surface of the body, as shown in FIG. 2B. In this configuration, a fraction of light from light source 206 is backscattered by the tissue into light detector 214.

Referring to FIG. 2C, if the PPG device is incorporated into a chronically implantable device 220 (e.g., an implantable cardioverter defibrillator (ICD), pacemaker, or any other implantable device), light source 206 and light detector 214 can be mounted adjacent to one another on the housing or header of the implantable device. Light source 206 and light detector 214 are preferably placed on the side of implantable device 220 that, following implantation, faces the chest wall, and are configured such that light cannot pass directly from the source to the detector. Thus, the reflection configuration is preferably used when the plethysmography device is implemented in an implantable device. The placement on the side of device 220 that faces the chest wall maximizes the signal to noise ratio by 1) directing the signal toward the highly vascularized musculature, and 2) shielding the source and detector from ambient light that enters the body through the skin. Alternatively, at the risk of increasing susceptibility to ambient light, light source 206 and light detector 214 can be placed on the face of the device that faces the skin of the patient. Additional details of an implantable PPG device are disclosed in U.S. Pat. No. 6,491,639 (Turcott), issued Dec. 10, 2002, entitled "Extravascular Hemodynamic Sensor," which is incorporated herein by reference.

Figure 3A:
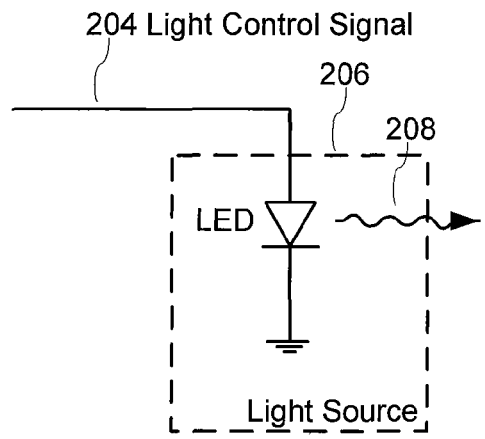
FIGS. 3A and 3B illustrate exemplary light sources for use in embodiments of the present invention.
Figure 3B:
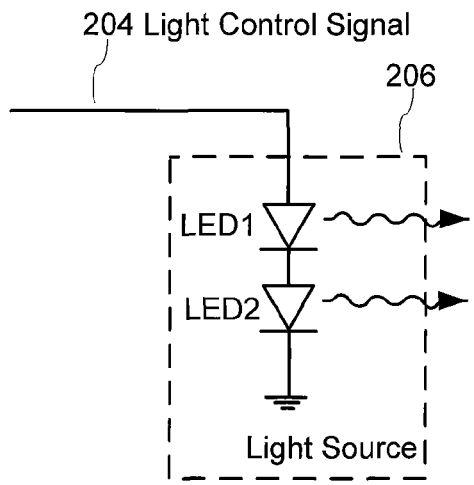

FIGS. 3A and 3B illustrate exemplary light sources for use in the embodiments of the present invention. Referring first to FIG. 3A, exemplary light source 206 includes a single LED that produces light signal 208. The LED can be, for example, a model L53SRC/F red LED, or a model L53F3C infrared LED, both manufactured by Kingbright Corporation, City of Industry, Calif. Referring to FIG. 3B, a series of LEDs (e.g., LED1 and LED2) can be used to increase the amount of optical power in light signal 208. Separate LEDs can be used. Alternatively, dual emitter combination LEDs can be used, such as model DLED-660/905-LL5-2, manufactured by UDT Sensors, Inc., Hawthorne, Calif. Light source 206 can be driven by a light control signal 204, as shown in FIGS. 2A, 3A and 3B. In a conventional plethysmography device, transmit light signal 208 would have a relatively constant average light intensity, though the light may be pulsed rapidly. Accordingly, in a conventional plethysmography device, light control signal 204 is relatively constant when averaged over a period of the pulse train.

One of ordinary skill in the art will appreciate that the use of other LEDs and other light sources (e.g., a laser diode) are within the spirit and scope of the present invention. Depending on the embodiment, light source 206 may or may not include additional elements that are used, for example, to maintain a relatively constant current through an LED.

Figure 4:
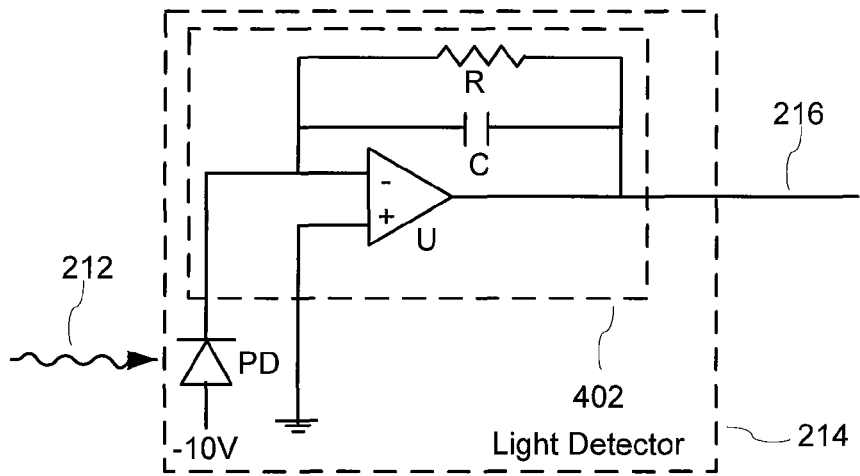
FIG. 4 illustrates an exemplary light detector for use in embodiments of the present invention.

FIG. 4 illustrates an exemplary light detector for use in embodiments of the present invention. Referring to FIG. 4, exemplary light detector 214 includes a photodiode PD operated in a current sensing photoconductive mode feeding a transimpedance amplifier 402. Photodiode PD can be, for example, a model PIN-4.0-LLS, manufactured by UDT Sensors, Inc. Transimpedance amplifier 402 includes a resistor R, a capacitor C and an operation amplifier U, such as model ALD1701, manufactured by Advanced Linear Devices, Inc., Sunnyvale, Calif. Amplifier 402, including the RC circuit, performs low pass filtering and provides gain. It also serves as an antialiasing filter if A/D conversion is applied directly to its output 216. One of ordinary skill in the art will appreciate that a photodiode PD can alternatively be operated in a voltage sensing configuration. Further, one of ordinary skill in the art will appreciate that the use of other photodiodes (e.g., an avalanche photodiode) and other light detectors (e.g., a photoresistor, a photodarlington, a phototransistor), are within the spirit and scope of the present invention. One of ordinary skill in the art will also appreciate that other amplifier configurations (e.g., an integrator amplifier or a transistor based amplifier) can be used in place of transimpedance amplifier 402 shown in FIG. 4. An integrated photodiode/amplifier (e.g., a Burr-Brown OPT101, available from Burr-Brown Corporation, Tucson, Ariz.) can also be used.

In a conventional PPG device (e.g., 200B), a constant average optical power is delivered by light source 206 (e.g., an LED) and plethysmograph information (e.g., measurements of waveform 102 shown in FIG. 1) is determined based on time varying optical power incident on light detector 214. A PPG device can alternatively adjust the source of optical power such that a relatively constant average light intensity is detected at a light detector, as described in commonly assigned U.S. Pat. No. 6,731,967 (Turcott), issued May 4, 2004, entitled "Methods and Devices for Vascular Plethysmography Via Modulation of Source Intensity," which is incorporated herein by reference. The time-varying modulating signal (e.g., that controls the source power) can then be used as the plethysmography signal (i.e., the information signal), rather than the time-varying detected optical power. The time-varying detected optical power is used (e.g., in a feedback loop) to adjust the source intensity. Use of this alternative type of plethysmography device, in accordance with an embodiment of the present invention, shall be explained in more detail below with reference to FIG. 6.

Figure 5:
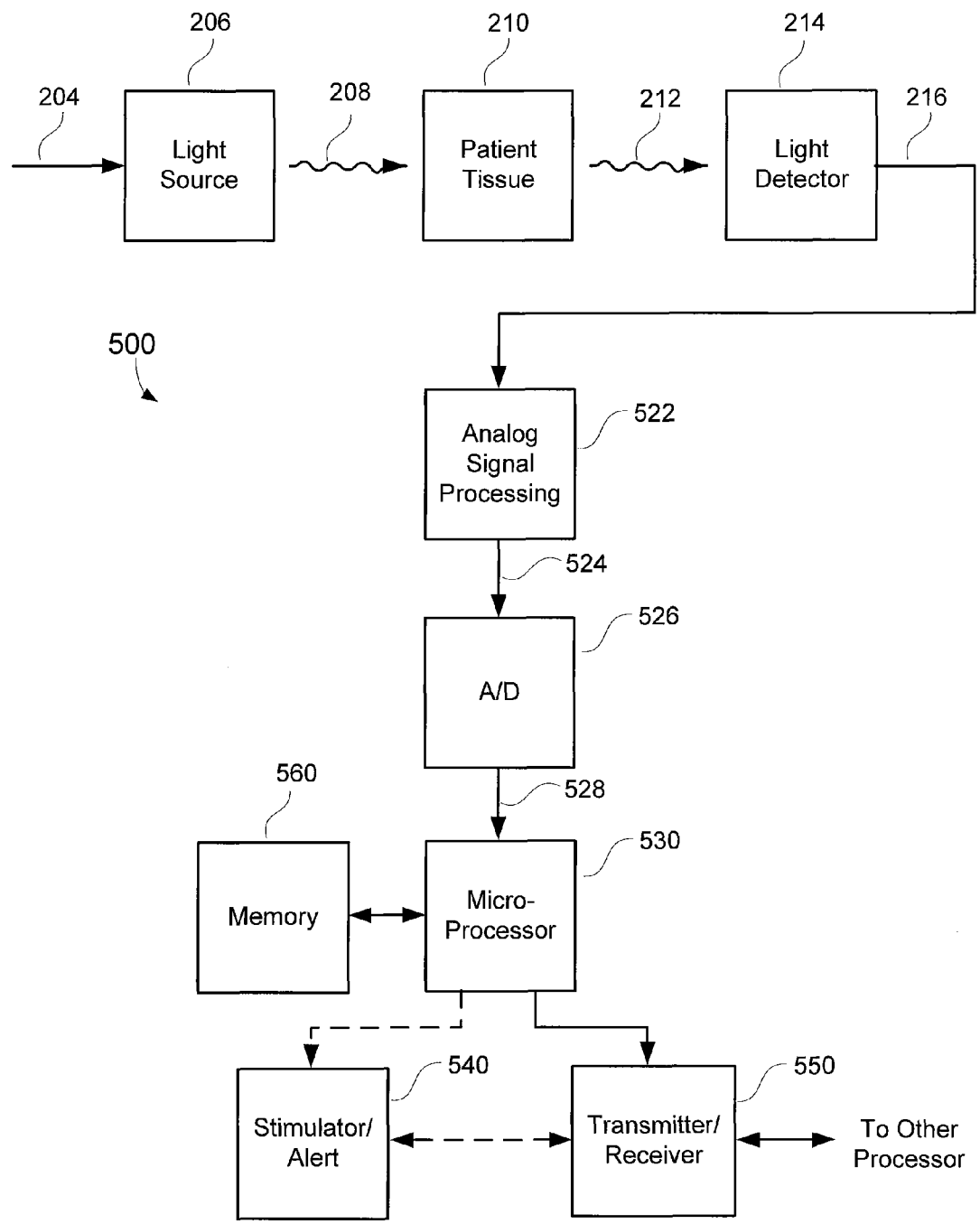
FIG. 5 illustrates an overview of a respiratory monitoring system according to an embodiment of the present invention.

FIG. 5 includes a block diagram that provides an overview of a respiratory monitor 500, according to an embodiment of the present invention. As will be explained in more detail below, monitor 500 can also be used for sleep apnea related analysis. Light source 206 outputs a transmit light signal 208 of substantially constant average light intensity (as controlled by light control signal 204). Light signal 208 is transmitted through and/or reflected by (depending on the embodiment) patient tissue 210. Receive light signal 212 is received by light detector 214. Changes in light intensity of the received light signal 212 are proportional to changes in blood volume in patient tissue 210. Light detector 214 produces a light detection signal 216 that is representative of the received light signal 212. Light output signal 216, which is likely an analog encoded information signal, is preferably filtered and amplified by an analog signal processor block 522. A filtered and amplified signal 524 is then provided to an analog to digital converted (A/D) 526, which provides a digital encoded plethysmography information signal 528 to a microprocessor 530.

Microprocessor 530 analyzes the encoded information signals 528. According to an embodiment of the present invention, microprocessor 530 analyzes the shape of the plethysmography signal represented by the encoded information signals 528. For example, microprocessor 530 can estimate arterial pulse amplitudes based on maximum and minimum values deciphered from the encoded information signals over durations of cardiac cycles.

If monitor 500 is not implanted, light source 206 and light detector 214 can be made small and can conveniently attach to a peripheral portion of the body, such as a finger, toe, or ear. Thus, patients are likely to tolerate regular use of these sensors for an extended period of time, such as during sleep each night. Particular embodiments include a finger cuff, a wristband, a configuration resembling a watch, and a configuration resembling a clip-on earring. Light source 206 and light detector 214 could be tethered to a larger unit containing the bulk of the electronic circuitry (e.g., microprocessor 530 and a memory 560). In this case, monitor 500 would be worn primarily when the patient is sleeping. Alternatively, data (e.g., from light detector 214, A/D 522, or microprocessor 530) could be continuously telemetered to a processor (e.g., microprocessor 530 or some other processor), which might be worn on the patient's clothing or located in the patient's home and/or office. In this case, the monitor could be worn both during sleep and during activity. Nevertheless, despite the cost advantages of an external embodiment, such an approach necessarily requires patient cooperation. Because of the disadvantages associated with this, as described above, it may be preferable that monitor 500 is an implanted extravascular configuration. However, it should be clear that many embodiments of the present invention are not limited to implantable implementations.

Monitor 500 can also include a transmitter/receiver 550 (i.e., a telemetric circuit) and a memory 560. If monitor 500 is chronically implanted, transmitter/receiver 550 enables the operating parameters of monitoring device 500 to be non-invasively programmed into the memory 560 through telemetric communications with an external device, such as a programmer or transtelephonic transceiver. Transmitter/receiver 550, which is preferably controlled by microcontroller 530, also enables monitor 500 to communicate with other types of external processors. For example, transmitter/receiver 550 enables plethysmography information (e.g., the values discussed above) and status information relating to the operation of device 500 (e.g., as contained in microcontroller 530 and/or memory 560) to be sent to an external device (e.g., a remote processor or diagnostic system analyzer) through an established communication link. Microprocessor 530 can produce HF assessment information, and transmitter/receiver 550 can transmit the information to another processor as appropriate. Transmitter/receiver 550 can additionally, or alternatively, transmit measured values and/or calculated values to an external device (e.g., a remote processor) that can assess respiration based on such values. Alternatively, the encoded information signals (e.g., light detection signal 216) can be transmitted directly to an external device (e.g., a remote processor), and the external device can perform appropriate measurements and calculations (individually and collectively referred to herein as "determinations").

For examples of a transmitter/receiver 550 (also known as a telemetric circuit) of a chronically implantable device, see U.S. Pat. No. 4,809,697, entitled "Interactive Programming and Diagnostic System for use with Implantable Pacemaker" (Causey, III et al.), and U.S. Pat. No. 4,944,299, entitled "High Speed Digital Telemetry System for Implantable Device" (Silvian), each of which is hereby incorporated herein by reference. Another example of a telemetric circuit for use in a chronically implantable device is the TR1000 transceiver manufactured by RF Monolithics, Dallas, Tex. The TR 1000 is a single-chip, low-power, 916.5 MHz transceiver. The operating frequency of 916.5 MHz is desirable because of the modest requirements on antenna size it imposes.

Monitor 500 can also include a stimulation/alert block 540, that informs a patient, physician, clinician and/or any other person (or processor) of the respiratory status of the patient. If monitor 500 is implanted, HF alert block 540 is preferably an external device that telemetrically communicates with microprocessor 530 (e.g., using transmitter/receiver 550). Stimulation/alert block 540 can include an indicator that provides, for example, an acoustic, mechanical vibration, optical and/or electrical indication and/or stimulation. Such an alert indicator can be triggered when a criterion (e.g., threshold) is satisfied (e.g., exceeded), as discussed below. In one embodiment stimulation/alert 540 includes an inductive coil that generates both sound and mechanical vibration. In an alternative embodiment, the function of stimulation/alert 540 is incorporated into microprocessor 530 and transmitter/receiver 550.

In monitor 500 described above, a relatively constant average optical power is delivered by light source 206 (e.g., an LED) and the plethysmograph signal is determined based on the time varying optical power incident on light detector 214. As previously mentioned, a PPG device can alternatively adjust the source of optical power such that a relatively constant average light intensity is detected at a light detector, as described in commonly assigned U.S. Pat. No. 6,731,967, which has been incorporated herein by reference above. The time-varying modulating signal (e.g., that controls the source power) can then be used as the plethysmography signal (i.e., the information signal), rather than the time-varying detected optical power. The time-varying detected optical power is used (e.g., in a feedback loop) to adjust the source intensity. Use of this alternative type of plethysmography device, in accordance with an embodiment of the present invention, shall now be described with reference to FIG. 6.

Figure 6:
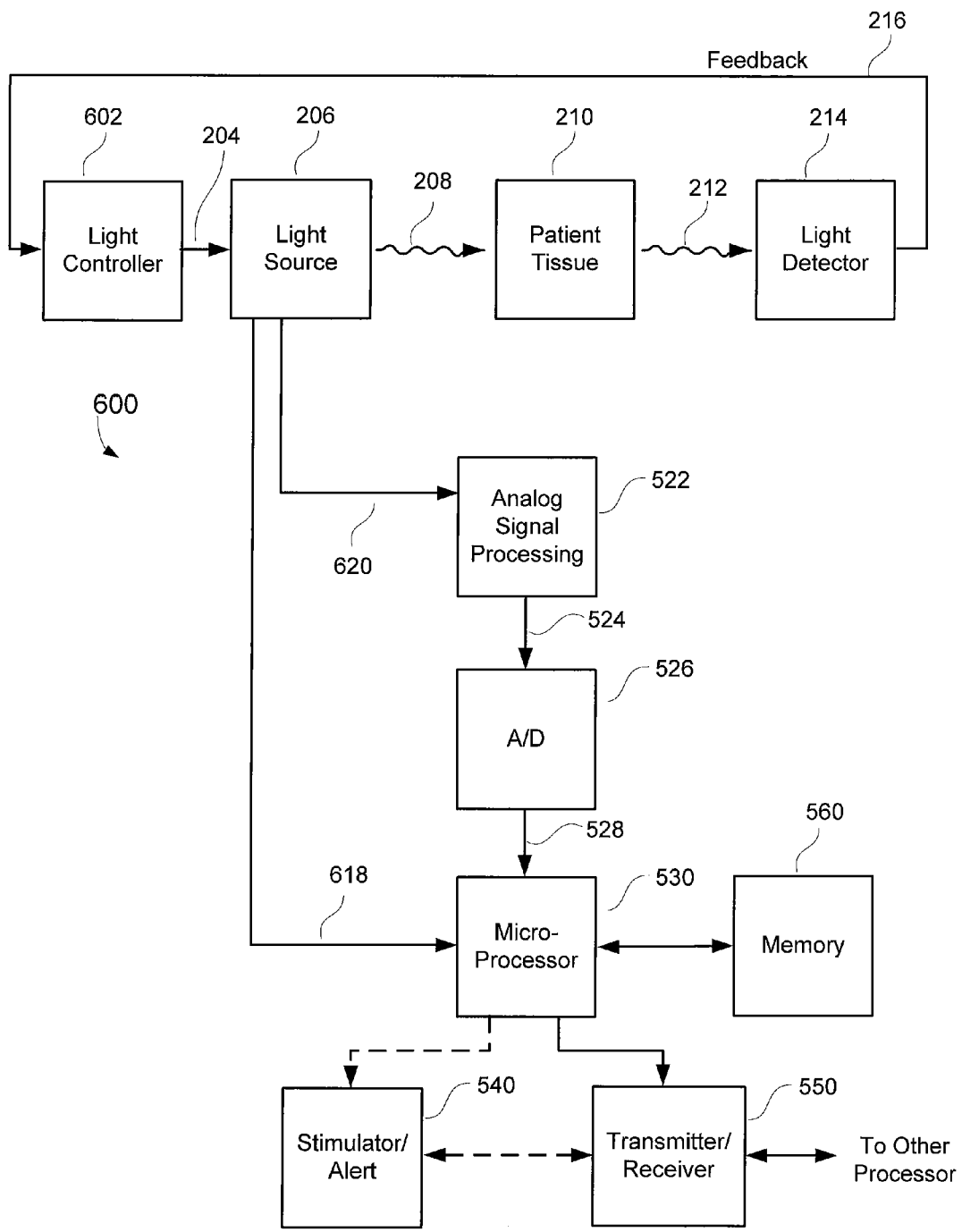
FIG. 6 illustrates an overview of a monitoring system according to an alternative embodiment of the present invention.

Referring to FIG. 6, a monitor 600 includes a light controller 602 that produces light control signal 204 that drives light source 206. Light source 206 outputs a transmit light signal 208 based on light control signal 204. Light signal 208 is transmitted through and/or reflected by (depending on the embodiment) patient tissue 210. A receive light signal 212 is received by a light detector 214.

Light detector 214 provides light detection signal 216 (also referred to, for this embodiment, as feedback signal 216) to light controller 602. Light controller 602 adjusts light control signal 204, based on a difference between feedback signal 216 and an internal reference signal, such that a relatively constant average light intensity is detected by light detector 214. Stated another way, light controller 602 adjusts light control signal 204 based on a difference between feedback signal 216 and a reference signal, such that the difference between feedback signal 216 and the reference signal is minimized.

In this embodiment, a time-varying modulating signal of light controller 602 is used as (or to produce) the plethysmography signal (i.e., the information signal), rather than the time-varying detected optical power. For example, in one embodiment, described below with reference to FIGS. 6 and 7, an analog output signal 620 is provided from the light controller 602. Analog output signal 620, which is likely an analog encoded information signal, is preferably filtered and amplified by analog signal processor block 522. A filtered and amplified signal 524 is then provided to an analog to digital converted (A/D) 526, which provides a digital encoded information signal 528 to microprocessor 530. In an alternative embodiment, light controller 602 digitally controls light source 206, and a digital plethysmography information signal 618 is provided directly to microprocessor 530. Microprocessor 530 analyzes the encoded information signals (e.g., 618 or 528).

Figure 7:
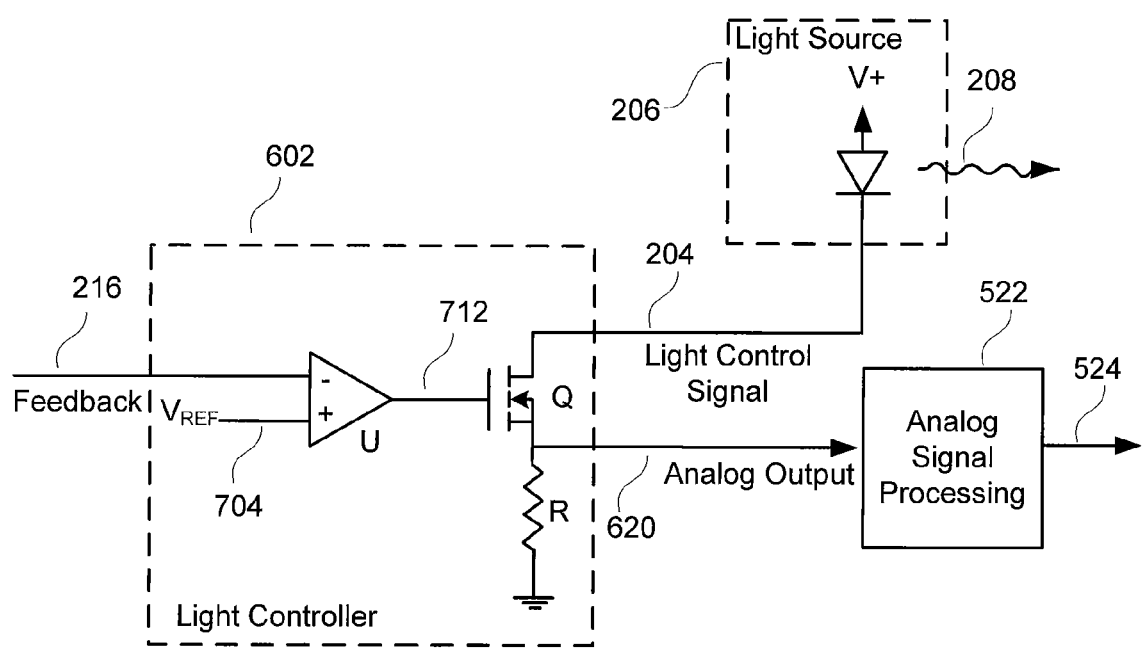
FIG. 7 illustrates additional details of the light detector of FIG. 6, in accordance with an embodiment of the present invention.

Referring now to FIG. 7, light controller 602 outputs light control signal 204, which drives light source 206. In this embodiment, light control signal 204 is an analog voltage or current signal having a variable voltage or current amplitude. More specifically, in this embodiment the amplitude of the light control signal 204 is adjusted (i.e., increased or decreased) by light controller 602, based on a difference between feedback signal 216 and a reference signal 704 so that a relatively constant average light intensity is detected by light detector 214 (See FIG. 6). Stated another way, light controller 602 adjusts the amplitude of light control signal 204, based on a difference between feedback signal 216 and a reference signal, such that the difference between feedback signal 216 and the reference signal is minimized.

In this implementation, light controller 602 includes a comparator 710 (e.g., operation amplifier U), which compares feedback signal 216 to a fixed reference voltage signal 704 (e.g., 1.2 volts). The term "comparator" is used herein to refer to a device that performs a comparison between two input signals and generates an analog or digital (e.g., binary) output based on the results of the comparison. In this embodiment, comparator 710 produces an analog output 712 based on the comparison. Light controller 602 also includes a transistor Q (e.g., a MOSFET transistor as shown). Transistor Q is controlled by analog output 712 (also referred to as comparison signal 712) of comparator 710. More specifically, transistor Q is turned on by an amount proportional to a difference between feedback signal 216 and fixed reference voltage signal 704. One of ordinary skill in the art will appreciate that various types of transistors, and/or various other types of current control circuits, can be used while still being within the spirit and scope of the present invention.

In this implementation, a modulated LED current, carrying the plethysmograph information, is sensed using a sense resistor R. More specifically, the information signal of interest, analog output 620 (which is the voltage across resistor R), is proportional to the LED current. As shown in FIG. 6, this signal 620 can be provided to analog signal processor 522, which filters and amplifies the signal. Filtered and amplified signal 524 can then be provided to A/D 526, which provides a digital encoded information signal 528 to microprocessor 530.

As mentioned above, alternatively and/or additionally, one or more digital output signals 618, which are digitally encoded information signals, are provided from light controller 602 to microprocessor 530. Additional details of such digital embodiments are described in U.S. Pat. No. 6,731,967, which was incorporated herein by reference above.

Figure 8:
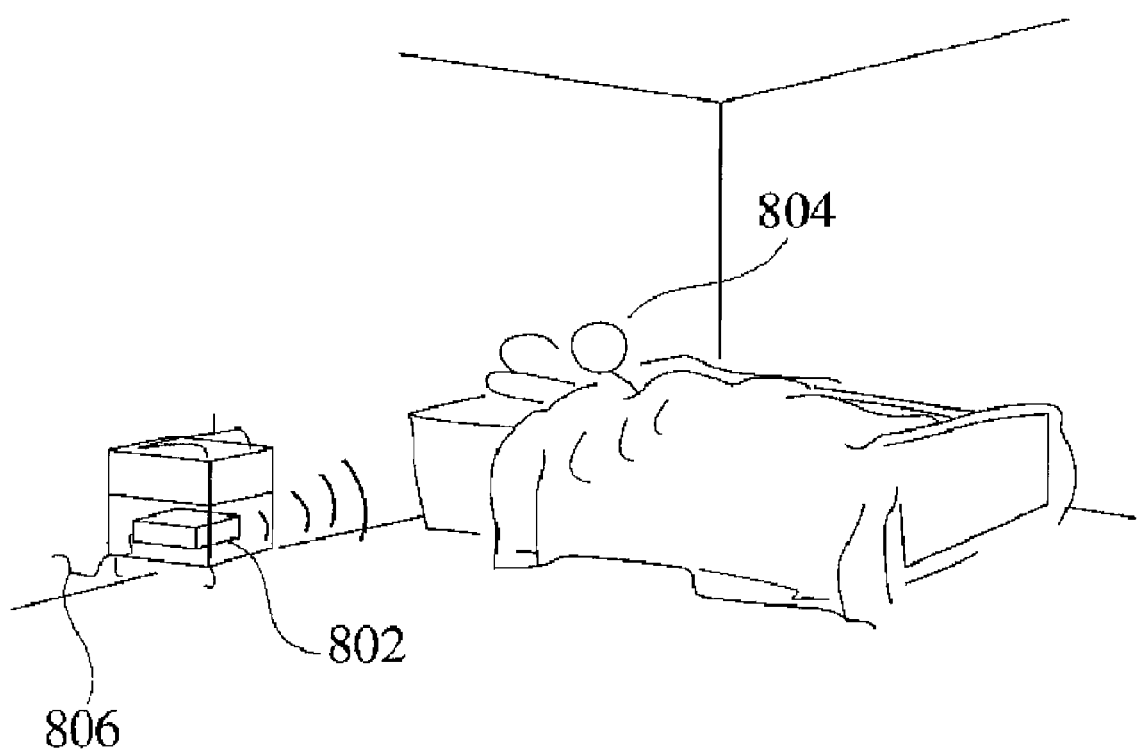
FIG. 8 illustrates placement of an external telemetry unit in, for example, a patient's bedroom.

FIG. 8 illustrates placement of an external telemetry (i.e., transmitter/receiver) unit 802 in, for example, the patient's bedroom. External telemetry unit 802, using telemetry at a distance, allows the transfer of data to and from monitor 500 if it is a chronically implanted device or a device that clips on the finger, toe or earlobe, without the active participation of the patient 804 or a clinician. External telemetry unit 802 is preferably positioned in a location(s) regularly frequented by the patient, such as the patient's bedroom, office, and/or automobile. External telemetry unit 802 can be in communication (e.g., through a telephone line 806, network connection and/or wireless links) with a central location for further processing or review (e.g., by a clinician).

Using PPG to Monitor Respiratory Factors

In accordance with embodiments of the present invention, a PPG sensor is used to monitor respirator rate, respiratory effort and/or oxygen saturation. Monitoring respiratory rate can include, e.g., detecting the absence and/or presence of respiration and/or detecting breaths per minute. Monitoring respiratory effort can include, e.g., detecting the volume of respiration (referred to as 'tidal volume') or the relative amount of intrathoracic pressure that is generated with respiration. Specifically, it has been discovered that as the intrathoracic pressure changes, there is a corresponding proportionate change in the amplitude of a PPG signal, which is indicative of respiratory effort. In many cases this is directly proportional to tidal volume. The monitoring of oxygen saturation can be conveniently performed using pulse oximetry, which uses two PPG signals, as will be briefly described below.

Figure 9:
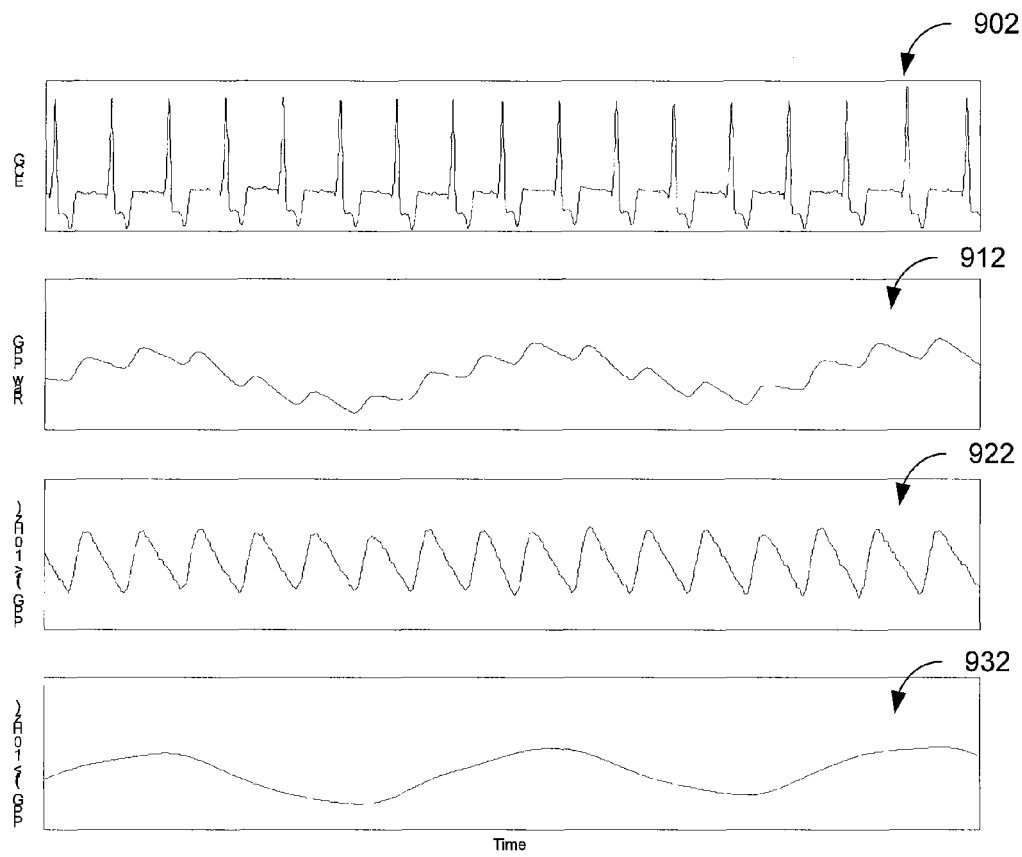
FIG. 9 illustrates an exemplary electrocardiogram signal, raw PPG signal, high pass filtered PPG signal and low pass filtered PPG signal.

FIG. 9 illustrates simultaneously recorded ECG and PPG signals, labeled 902 and 912, respectively. In this plot, a positive deflection of the PPG signal 912 is caused by increased light absorption by the tissue, and a corresponding decrease in detected light, as when a cardiac pulse causes an expansion of peripheral vascular volume. Conversely, a negative deflection of the PPG waveform results from a decrease in tissue light absorption, and a corresponding increase in detected light, as when vascular volume is reduced. Slow oscillation in the baseline of the PPG signal 912 is due to changes in intrathoracic pressure due to respiration, and likely results from both the modulation of peripheral venous volume induced by the changing intrathoracic pressure, and the modulation of the arterial volume secondary to ventilation-induced changes in arterial pressure (not shown). Of lower amplitude in this example, but still clearly apparent, are the pulsations in the PPG waveform 912 due to the arrival of the cardiac pulse at the periphery. Thus, effects arising from the modulation of both arterial and venous vascular volumes can be seen in the raw PPG signal 912.

Referring back to FIGS. 2A, 4 and 5, the PPG signal 912 is an example of the varying analog voltage light detection signal 216 that is produced by the light detector 214. Referring back to FIGS. 6 and 7, the PPG signal 912 can also be an example of the analog output signal 620.

FIG. 9 also illustrates the PPG signal 912 after it is high-pass filtered and low-pass filtered, with the high- and low-pass filtered signals respectively labeled 922 and 932. The exemplary cut-off frequency for the high and low pass filtering is 1.0 Hz. Signals 922 and 932 are useful for showing that the respiration-associated low frequency portion of the PPG signal can be easily separated from the high frequency cardiac component.

Respiratory rate can be determined, e.g., by sampling a PPG signal (preferably, but not necessarily, after low pass filtering of the PPG signal) to thereby produce a plurality of samples of the PPG signal. An average of the plurality of samples can then be determined, so that the average can serve as a threshold. Then, the plurality of samples can be compared to the average to thereby determine a number of threshold crossings. The rate of respiration (e.g., breaths per minute) can then be determined based on the number of threshold crossings, e.g., by counting the number of crossings from above the threshold to below the threshold (or vice versa) for the window of time, and converting that number to a conventional scale, such as breaths per minute. Another way to accomplish this is to determine an average of the plurality of samples. Then, the plurality of samples can be normalized by subtracting the average from each of the plurality of samples, to thereby produce a plurality of normalized samples. The plurality of normalized samples can then be compared to zero to thereby determine a number of zero crossings. Then, in a similar manner to that just described, the rate of respiration can be determined based on the number of zero crossings. In another alternative, a nonzero offset is added and subtracted to the average PPG value, yielding two thresholds. A respiratory cycle is counted when the PPG signal makes the transition from one of the thresholds (e.g., the more positive threshold) to the other. Thus, only respirations of sufficiently large respiratory effort will be counted in the rate calculation. This has the advantage of avoiding the inadvertent counting of noise as a respiratory cycle when the respiratory effort is small, as with severe hypopnea or CSA.

Spectral methods can also be used to measure respiratory rate based on the PPG signal. For example, a frequency spectrum can be produced for a PPG signal. The peak respiratory frequency can then be observed from the spectrum.

Specifically, observable changes in a PPG signal due to respiratory effort include amplitude changes (e.g., peak-to-peak amplitude, positive amplitude or negative amplitude) over time. In accordance with an embodiment of the present invention, respiratory effort can be determined by sampling the PPG signal (preferably, but not necessarily, after high pass filtering the PPG signal) and determining an amplitude from the plurality of samples of the PPG signal. This can be accomplished, e.g., by determining a positive amplitude, negative amplitude and/or peak-to-peak amplitude based on the plurality of samples. The amplitude is indicative of the respiratory effort in that an increase in amplitude is indicative of an increased respiratory effort, and a decrease in amplitude is indicative of a decrease in respiratory effort.

An area under a curve is typically proportional to an amplitude of a signal. Thus, amplitudes of a PPG signal could also be measured indirectly by measuring area under a curve (e.g., the signal could be rectified about its average value and then the total area under the curve can be measured).

In accordance with another embodiment, digital and/or analog peak detectors can also be used to measure peak amplitudes. For example, if peak-to-peak amplitudes are desired, a first analog peak detector can be used to measure maximum peak amplitudes, while a second analog peak detector can be used to measure minimum peak amplitudes. The amplitudes stored by the peak detectors can then be sampled and converted to digital data using an analog-to-digital converter. A single peak-detector may also be sufficient if only positive or negative amplitudes are being measured.

Pulse oximetry is a well-known technique for producing measures of blood oxygen saturation levels using two PPG signals. Typically, a pair of LEDs are used to produce light of two different wavelengths, typically red (e.g., about 660 nm wavelength) and infrared or near infrared (e.g., about 940 nm wavelength), which are transmitted through or reflected by patient tissue such that a single light detector receives incident light that alternates between red and infrared light. The LEDs are serially pulsed to produce an interleaved signal stream that is transmitted through or reflected from tissue of a patient. As the light passes through and/or is reflected from tissue, some of the energy is absorbed by arterial and venous blood, tissue and the variable pulsations of arterial blood. The interleaved red and infrared light stream is received by the single light detector, which produces a first PPG signal based on the red light stream and a second PPG signal based on the infrared light stream. The amplitudes of the red light pulses in the light stream are differently effected by the absorption than the infrared light pulses, with the absorptions levels depending on the oxygen saturation level of the blood.

Using electronic circuitry, firmware and/or software, the received light signals in the infrared and red wavelengths are analyzed so that oxygen saturation levels can be determined. At a high level, demultiplexing is used to produce a signal path for the received red light and a separate signal path from the received infrared light. Each signal path will typically include one or more filters and an A/D converter to sample the received light signals. The samples of the red light signal are then used to determine the DC offset (i.e., average) and pulse amplitude of the received red light. Similarly, the samples of the infrared light signal are then used to determine the DC offset (i.e., average) and pulse amplitude of the received infrared light. Each pulse amplitude is then normalized (e.g., by dividing the pulse amplitude by the corresponding DC offset) and a ratio of the red-to-infrared light is determined by dividing the normalized red pulse amplitude by the normalized infrared pulse amplitude. Then, a look-up table is typically used to determine the oxygen saturation level. A look-up table is typically used because for a given optical sensor there is a one-to-one correspondence between the red-to-infrared ratios and O2 saturation levels.

Monitoring Respiratory Disorders

Embodiments of the present invention will now be further described with reference to the high level flow diagram of FIG. 10.

Figure 10:
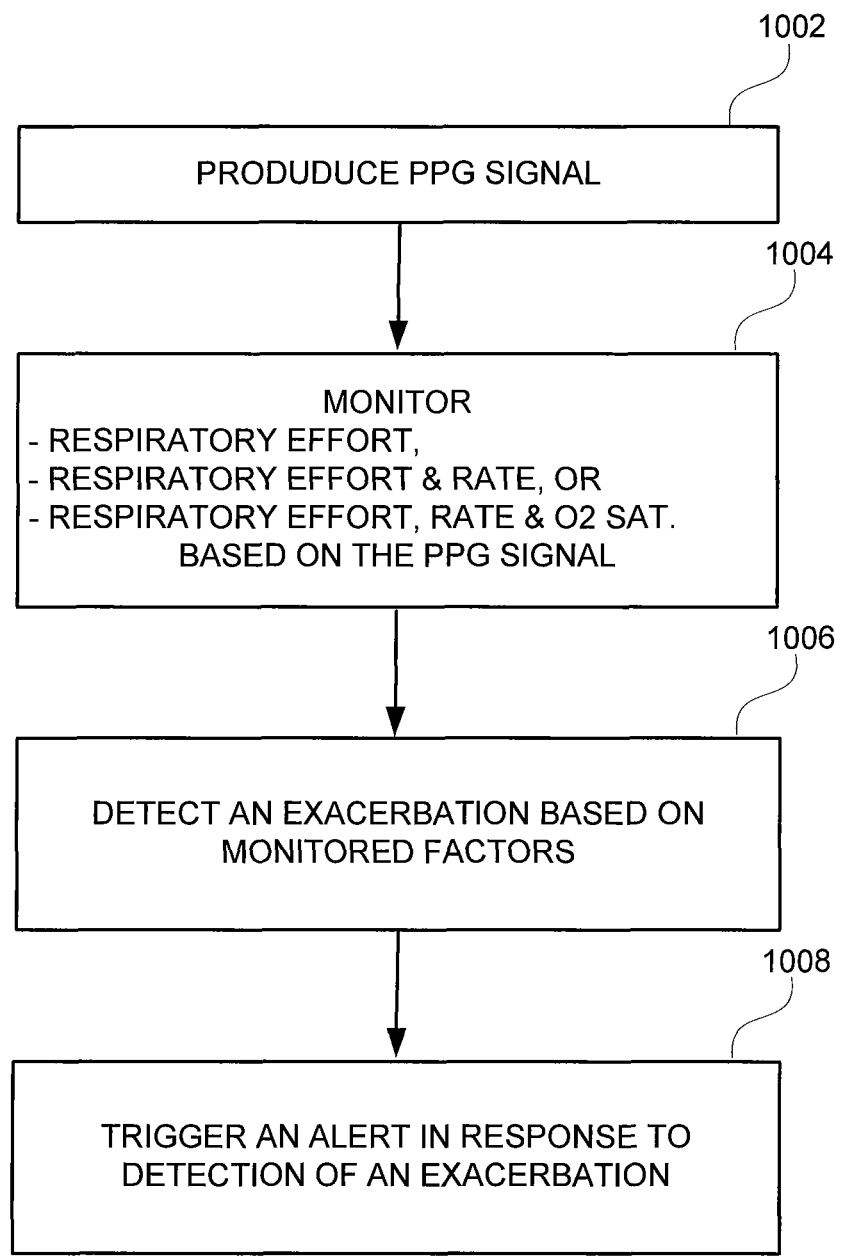
FIG. 10 is a high level flow diagram that is useful for explaining embodiments of the present invention.

Referring to FIG. 10, at a step 1002, a PPG signal that is representative of peripheral blood volume is produced. This can be performed using a PPG sensor, examples of which have been described in detail above. The PPG sensor can be chronically implanted in a patient. Alternatively, the PPG sensor is not implanted in a patient, but is rather implemented as a device that is placed against or attaches to a peripheral portion of a patient's body, as has been described above.

At a step 1004, factors that may provide information relating to the respiratory disorder are monitored, based on the PPG signal. As mentioned above, the disorders that can be monitored include, but are not limited to, asthma, emphysema and sleep apnea. Assuming the device is chronically implanted, the monitored factors can be immediately analyzed within the implanted device, stored for later analysis within the implanted device, immediately transmitted to an external device that can analyze the monitored factors (e.g., using telemetry, as explained above) and/or stored within the implanted device for later transmission to an external device. Assuming the device is not implanted, the monitored factors can be immediately analyzed and/or stored for later analysis.

In accordance with an embodiment of the present invention, step 1004 includes monitoring respiratory effort based on the PPG signal. As discussed above, respiratory effort can be monitored by determining amplitudes of the PPG signal, with increases in amplitude representing increases in respiratory effort, and decreases in amplitude representing decreases in respiratory effort.

In accordance with an embodiment of the present invention, a step 1006 includes detecting an exacerbation of the respiratory disorder based on the monitored respiratory effort. For example, if the respiratory disorder being monitored is asthma, then respiratory effort will increase during an exacerbation (i.e., during an asthma attack). This can be detected by comparing amplitudes of the PPG signal to a threshold, and determining whether a threshold is exceeded. The threshold can be a predetermined value. Alternatively, the threshold can be a value that is based on amplitudes previously measured during normal respiratory periods. For example, the threshold can be set at 130% of the amplitudes that are measured during normal respiratory periods. These are just a few examples of how a threshold can be defined, which are not meant to be limiting.

Referring back to step 1004, respiratory rate can also be monitored based on the PPG signal. This can be accomplished, as described above, by counting threshold crossings and/or analyzing a frequency spectrum of the PPG signal. The information relating to monitored respiratory effort and rate can be analyzed immediately, stored for later analysis, etc. Then, step 1006 can include detecting an exacerbation based on both respiratory effort and respiratory rate. For example, if the respiratory disorder being monitored is asthma, then respiratory effort and respiratory rate will both increase during an asthma attack. Accordingly, detected amplitudes and frequency can be compared to respective thresholds at step 1006. The threshold for respiratory rate can be predetermined, set based on a percentage of a patient's normal rate (e.g., 200% of a normal rate), etc. An exacerbation can then be detected if the monitored respiratory rate exceeds its corresponding threshold, and the monitored respiratory effort exceeds its corresponding threshold.

Then, at a step 1008, an alert indicator can be triggered in response to the exacerbation being detected. For example, if the PPG sensor is implanted in or attached to a periphery of a child, the alert indicator may inform a school nurse, a parent or a physician of the exacerbation.

Returning back to step 1004, blood oxygen saturation can also be monitored based on the PPG signal. This can be accomplished if two PPG signals are produced at step 1004, e.g., one produced using red light, and the other produced using infrared or near infrared light. More specifically, pulse oximetry, which is well known in the art, and has been briefly discussed above, can be used to measure blood oxygen saturation levels. Then, step 1006 can include detecting an exacerbation based on monitored respiratory effort and blood oxygen saturation level. Step 1006 can alternatively include detecting an exacerbation based on monitored respiratory effort, respiratory rate and blood oxygen saturation. As with the other factors, there can exist a threshold for blood oxygen saturation level. If the respiratory disorder being monitored is asthma, blood oxygen saturation levels should decrease during an asthma attack.

In the above discussed manners, embodiments of the present invention can be used to monitor, detect, diagnose asthma as well as observe the success and fine tuning of treatments of asthma. The device used to produce the PPG signal can be implanted as explained above. Alternatively, the device can be a ring, cuff, clip, etc. that a patient can easily wear while walking around.

In accordance with embodiments of the present invention, step 1002 is performed while a patient is sleeping so that a patient's sleep apnea can be monitored. In this embodiment, step 1004 can include monitoring respiratory effort, by determining amplitudes of the produced PPG signal. Then at step 1006, an episode of sleep apnea can be detected based on the measured amplitudes. It is noted that the term apnea used herein is also meant to include hypopnea, which is generally define as decrease in airflow by at least 50% for ten seconds or more (as opposed to a substantially complete cessation of airflow). For example, if the patient experiences a CSA episode, there will be substantially no respiratory effort and, and thus a significant decrease in the determined amplitudes of the PPG signal. If the patient experiences an OSA episode, there will be continued respiratory effort during the apneic period, which will be observable from determined amplitudes of the PPG signal. If the patient experiences an episode of hypopnea, respiratory effort continues during the period of hypopnea, which are recognizable as decreased in the respiratory pulse amplitude of the PPG signal, but not to the extent of as during OSA or CSA. Besides detecting periods of apnea, the monitored respiratory effort based on the PPG signal (alone, or in combination with monitored blood oxygen saturation level and/or respiratory rate) can also be used to diagnose a type of apnea that a patient is suffering from, because CSA, OSA and hypopnea typically will effect the amplitudes of a PPG signal differently (as well as effect blood oxygen saturation levels and respiratory rate differently). Additionally, the monitored respiratory effort based on the PPG signal can also be used to determine if treatments for a patient's apnea are working, and/or to determine if the treatments can be fine tuned.

Figure 11A:
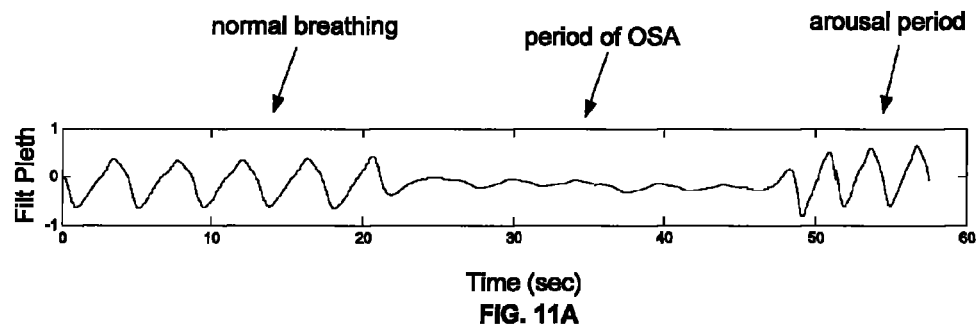
FIGS. 11A, 11B and 11C illustrates exemplary low pass filtered PPG signals for various types of episodes of sleep apnea.

FIG. 11A illustrates an exemplary PPG signal which includes a portion corresponding to normal respiration, followed by a portion corresponding to an apneic period due to OSA, followed by an arousal period. During OSA there is continued respiratory effort, and thus, while the amplitudes of the PPG signal may decrease, pulses corresponding to changes in arterial blood pressure (due to the respiratory effort) are still recognizable in the PPG signal. The blood oxygen saturation level will be very low during the apneic period due to OSA. Respiratory rate, effort and blood oxygen saturation level will increase during the arousal period as the patient gasps for air.

Figure 11B:
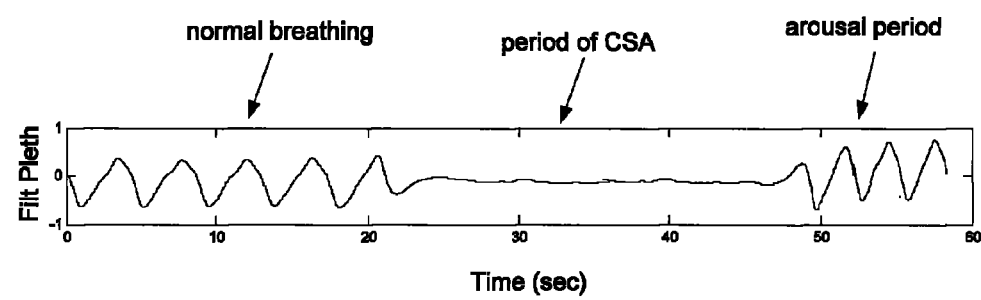

FIG. 11B illustrates an exemplary PPG signal which includes a portion corresponding to normal respiration, followed by a portion corresponding to an apneic period due to CSA, followed by a portion corresponding to an arousal period. During CSA there is no respiratory effort and substantially no respiratory rate, which can be recognized by a substantially flat lined PPG signal due to substantially no changes in arterial blood pressure. The blood oxygen saturation level will be very low during the apneic period due to CSA. Respiratory rate, effort and blood oxygen saturation level will then increase during the arousal period as the patient gasps for air.

Figure 11C:
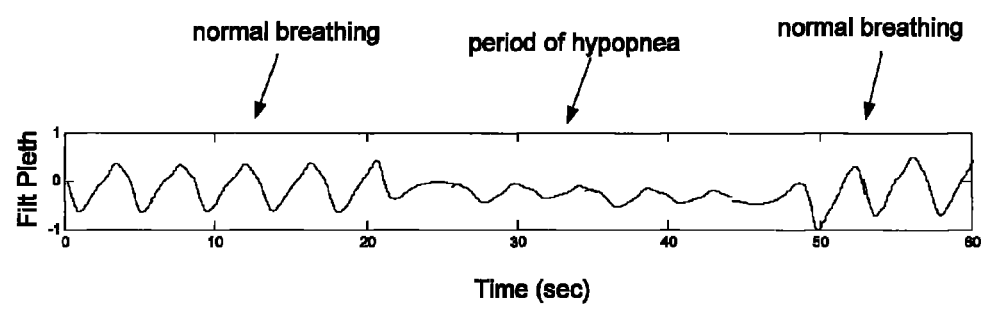

FIG. 11C illustrates an exemplary PPG signal which includes a portion corresponding to normal respiration, followed by a portion corresponding to an apneic period due to hypopnea, followed by a portion corresponding to a return to normal respiration. During hypopnea, there is continued respiratory effort, and thus, while the amplitudes of the PPG signal may decrease, pulses corresponding to changes in arterial blood pressure (due to the respiratory effort) are still recognizable in the PPG signal. As mentioned above, the blood oxygen saturation level will drop somewhat during the apneic period due to hypopnea, but not to the extent as during CSA of OSA.

It is noted that FIGS. 11A-11C are not actual signals obtained from patient measurements, but rather are signals that have been drawn to show how different types of apnea may affect a PPG signal differently.

In accordance with embodiments of the present invention, in addition to monitoring the respiratory effort (of a patient that is sleeping) based on the PPG signal, step 1004 can also include monitoring respiratory rate and/or blood oxygen saturation level based on the PPG signal. This will provide more information about the sleep apnea, which can be used to even better detect apneic period at step 1006, to better diagnose a type of apnea and/or to better determine if specific treatments are working. For example, if a patient experiences a CSA episode, the monitored respiratory effort, rate and blood oxygen saturation level based on the PPG signal should approach zero, but then all increase when the patient gasps for air. If a patient experiences an OSA episode, the patient will still be trying to breathe, so the monitored respiratory rate may initially decrease but not to the extent of CSA, and then increase as the patient grasps for air. During OSA, the monitored oxygen saturation level should significantly fall. If a patient experiences an episode of hypopnea, then the monitored respiratory rate based on the PPG signal should not significantly drop, since hypopnea is associated with breaths becoming more shallow. During hypopnea the monitored blood oxygen saturation level should drop, but not to the extent it would during a period of CSA or OSA.

In accordance with embodiments of the present invention, a patient can be stimulated in response to a specific type of apnea being detected. Such a stimulation can be, e.g., an electrical stimulation, an audible stimulation or a vibrating stimulation. The purpose of the stimulation would be to arouse the patient enough such that they begin a normal breathing pattern (e.g., by bringing them to a lighter state of sleep), preferably without completely waking the patient. If the device that produces the PPG signal and measures aspects of the PPG signal is implanted, then the stimulation can be produced from within the patient by the implanted device housing the PPG sensor. Alternatively, an implanted device can trigger an non-implanted device (e.g., using telemetry) to provide the stimulation. In another embodiment, where the device the produces the PPG signal and/or measures aspects of the PPG signal is not implanted, the non-implanted device can provide the stimulation, or direct a further non-implanted device to provide the stimulation.

In the above discussed manners, embodiments of the present invention can be used to monitor, detect and diagnose sleep apneas, as well as observe the success and fine tuning of treatments of sleep apneas. The device used to produce the PPG signal can be implanted as explained above. Alternatively, the device can be a ring, cuff, clip, etc. that a patient can easily wear while sleeping at home. Thus, embodiments of the present invention can be used to reduce and hopefully avoid patient stays in sleep clinics, thus reducing medical costs and inconveniences.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. A method of monitoring respiration comprising:
   obtaining a photoplethysmography (PPG) signal that is representative of blood volume;
   determining an average of the PPG signal;
   adding an offset to the average to produce a first threshold;
   subtracting the offset from the average to produce a second threshold; and
   monitoring respiratory rate by determining a number of transitions from one of the first and second thresholds to another of the first and second thresholds.

2. The method of claim 1 wherein obtaining the PPG signal comprises producing the PPG signal while a patient, whose respiratory disorder is being monitored, is sleeping.

3. The method of claim 2 further comprising:
   monitoring respiratory effort by determining amplitudes of the PPG signal; and
   detecting an episode of sleep apnea based on the respiratory effort.

4. The method of claim 3 further comprising:
   monitoring blood oxygen saturation level based on the PPG signal; and
   wherein detecting an episode of sleep apnea based on respiratory effort comprises detecting an episode of sleep apnea based on the respiratory effort and blood oxygen saturation level.

5. The method of claim 4 wherein detecting an episode of sleep apnea based on respiratory effort comprises detecting an episode of sleep apnea based on the respiratory rate, respiratory effort and blood oxygen saturation level.

6. The method of claim 3 wherein detecting an episode of sleep apnea based on the monitored-respiratory effort that is monitored, further comprises detecting an episode of sleep apnea based on the respiratory rate and respiratory effort.

7. The method of claim 1 further comprising:
   monitoring respiratory effort by determining amplitudes of the PPG signal; and
   detecting an exacerbation of a respiratory disorder based on respiratory effort and respiratory rate.

8. The method of claim 7 wherein the respiratory disorder is asthma, and wherein detecting an exacerbation comprises detecting an asthmatic episode based on the respiratory rate and respiratory effort.

9. The method of claim 8 wherein detecting an exacerbation comprises detecting an asthmatic episode by comparing the respiratory rate to the first threshold and the respiratory effort to the second threshold.

10. The method of claim 7 wherein the respiratory disorder is asthma, and wherein detecting an exacerbation comprises detecting an asthmatic episode by comparing the respiratory effort to a threshold.

11. The method of claim 1 further comprising:
    monitoring respiratory effort by determining amplitudes of the PPG signal;
    monitoring blood oxygen saturation level based on the PPG signal;
    detecting an exacerbation of a respiratory disorder based on respiratory effort and blood oxygen saturation level.

12. The method of claim 11 wherein the respiratory disorder is asthma.

13. The method of claim 12 wherein detecting an exacerbation comprises detecting an asthmatic episode by comparing the respiratory rate to the first threshold, the respiratory effort to the second threshold and the oxygen saturation level to a third threshold.

14. The method of claim 11 wherein detecting an exacerbation of a respiratory disorder based on respiratory effort and blood oxygen saturation level comprises detecting an exacerbation of a respiratory disorder based on the respiratory effort, respiratory rate and blood oxygen saturation level.

15. A method of detecting episodes of sleep apnea, and distinguishing between hypopnea, obstructive sleep apnea (OSA) and central sleep apnea (CSA), said method comprising:
    obtaining a photoplethysmography (PPG) signal that is representative of a patient's peripheral blood volume;
    monitoring respiratory effort and respiratory rate based on the PPG signal;
    detecting an episode of sleep apnea based on at least one of the respiratory effort and respiratory rate that are monitored; and
    distinguishing between hypopnea, OSA and CSA, for a detected episode of sleep apnea, based on the respiratory effort and respiratory rate.

16. The method of claim 15 further comprising monitoring blood oxygen saturation level of a patient based on the PPG signal.

17. The method of claim 16 wherein detecting an episode of sleep apnea comprises detecting an episode of sleep apnea based at least two of the respiratory effort, respiratory rate and blood oxygen saturation level.

18. The method of claim 16 wherein distinguishing between hypopnea, OSA and CSA, for a detected episode of sleep apnea, comprises distinguishing between hypopnea, OSA and CSA based on the respiratory effort, respiratory rate and blood oxygen saturation level.

* * * * *